United States Patent [19]

Wilk

[11] Patent Number: 5,546,955
[45] Date of Patent: Aug. 20, 1996

[54] MEDICAL STOCKING FOR TEMPERATURE DETECTION

[76] Inventor: Peter J. Wilk, 185 West End Ave., New York, N.Y. 10023

[21] Appl. No.: 217,371

[22] Filed: Mar. 24, 1994

Related U.S. Application Data

[63] Continuation-in-part of Ser. No. 900,848, Jun. 18, 1992, abandoned.

[51] Int. Cl.⁶ .......................................... A61B 5/00
[52] U.S. Cl. ............................................ 128/736; 128/779
[58] Field of Search ................................ 128/736, 779; 602/1, 5, 13, 23

[56] References Cited

U.S. PATENT DOCUMENTS

| | | | |
|---|---|---|---|
| 2,531,074 | 11/1950 | Miller | 602/13 X |
| 3,651,694 | 3/1972 | Lamb | 128/738 |
| 3,830,224 | 8/1974 | Vanzetti et al. | 128/736 |
| 4,152,748 | 5/1979 | Arkans | 128/779 X |
| 4,379,461 | 4/1983 | Nilsson et al. | 128/736 |
| 4,416,552 | 11/1983 | Hessemer, Jr. et al. | 128/736 X |
| 4,771,791 | 9/1988 | Kubochi | 128/736 |
| 5,288,286 | 2/1994 | Davis et al. | 602/5 X |
| 5,293,876 | 3/1994 | Koltringer | 128/736 |

FOREIGN PATENT DOCUMENTS

| | | | |
|---|---|---|---|
| 2606630 | 5/1988 | France | 602/23 |
| 3904643 | 8/1990 | Germany | 128/736 |

*Primary Examiner*—Sam Rimell
*Attorney, Agent, or Firm*—R. Neil Sudol; Henry D. Coleman

[57] ABSTRACT

A hospital-type medical stocking is provided with a temperature sensor and an indicator operatively connected to the sensor for providing a signal indicative of leg temperature. The stocking is additionally provided with at least one strip of soft but substantially rigid material for inhibiting a rolling down of the stocking. The strip extends longitudinally along the stocking from an edge of the stocking's mouth. In addition, a pressure application component is provided on the stocking for automatically applying periodic compressive pressure to the person's leg.

28 Claims, 3 Drawing Sheets

MEDICAL STOCKING FOR TEMPERATURE DETECTION

CROSS-REFERENCE TO A RELATED APPLICATION

This application is a continuation-in-part of application Ser. No. 07/900,848 filed Jun. 18, 1992, now abandoned.

BACKGROUND OF THE INVENTION

This invention relates to a medical stocking. This invention more particularly relates to a stocking with components for use in diagnosing such medical conditions as phlebitis. This invention also relates to a hospital type stocking with a component for inhibiting stocking rolldown. In addition, this invention relates to a hospital type stocking with components for preventing or reducing venous stasis.

Patients in hospitals are generally required to wear compression stockings. Compression stockings are designed to exert a compressive pressure all around the wearer's leg in part for purposes of increasing interstitial tissue pressure in the leg, thereby reducing the outflow of plasma from the blood vessels. Excessive plasma outflow results in edema.

One difficulty with attempting to keep hospital patients in compression stockings is that the stockings exhibit a tendency to roll down. Inasmuch as many patients are elderly, senile, mentally disoriented, or otherwise incapable of maintaining the stockings properly rolled up, hospital personnel must attend to the patients' attire. However, it is well known that hospital personnel are overworked and have little time or inclination to continually pull up patients' socks.

One of the general purposes of compression stockings is to aid in venal circulation. Venous stasis, the failure of proper blood flow through the veins, is a potentially dangerous condition for many hospital patients. Clots may form in the blood, choking circulation and resulting in phlebitis. Clots must be removed, for example, through surgery.

Venous stasis is obviated during operations by wrapping the patient's legs in plastic sheet material which have cavities pressurized by a pump placed, for example, on the floor of the operating room.

OBJECTS OF THE INVENTION

An object of the present invention is to provide a medical stocking which has a reduced tendency to roll down.

Another object of the present invention is to provide a medical stocking with components for use in diagnosing such medical conditions as phlebitis.

Another, more particular, object of the present invention is to provide a medical stocking with components for preventing or reducing venous stasis.

Other objects of the present invention will be apparent from the detailed descriptions and drawings included herein.

SUMMARY OF THE INVENTION

A medical diagnostic device comprises, in accordance with the present invention, a sensor array for detecting temperature at a plurality of relatively spaced points on a person's leg, an attachment element attachable to a person's leg for maintaining the sensor array in operative juxtaposition with the person's leg, the sensor array being mounted to the attachment element, and an indicator operatively connected to the sensor array and to the attachment element for providing a signal indicative of a local rise in leg temperature at one of the measurement points relative to another of the measurement points, thereby providing an alert as to possible phlebitis in the leg.

According to another feature of the present invention, the diagnostic device further comprises a comparator operatively connected to the sensor array and the indicator for comparing a temperature detected by the sensor array at the one measurement point with a temperature detected by the sensor array at another measurement point. More particularly, the comparator may include comparison componentry for comparing the temperature detected by the sensor array at the one measurement point with a plurality of other temperatures measured by the sensor array at a plurality of other measurement points on the person's leg. The comparison componentry may include means for comparing the temperature detected by the sensor array at the one measurement point with each of the other temperatures individually. Alternatively, the diagnostic device may include a calculating circuit operatively connected to the sensor array and the indicator for determining an average value of a plurality of temperatures detected by the sensor array at a plurality of respective measurement points, the comparator including comparison componentry for comparing the temperature detected by the sensor array at the one measurement point with the calculated average value.

According to another feature of the present invention, the attachment element includes a flexible membrane attachable to the person's leg. The membrane preferably takes the form of a stocking. In that event, the stocking may be provided with a strip of soft but substantially rigid polymeric material, extending, for example, longitudinally along the stocking from an edge of a mouth opening thereof, for inhibiting a rolling down of the stocking.

According to another feature of the present invention, the membrane or stocking may be provided with components for automatically applying periodic compressive pressure to the person's leg. That componentry may include at least one chamber and means for pressurizing the chamber with a fluid. In the event that the membrane includes an outer layer of relatively inelastic material, pressurization of the chamber directs compressive force inwardly upon the person's leg.

According to another feature of the present invention, the indicator generates a visual and/or an audible alarm signal.

A medical diagnostic method utilizes, in accordance with one conceptualization of the present invention, a medical stocking with a sensor array mounted to the stocking for detecting temperature of a person's leg to which the stocking is fitted, the stocking also carrying an indicator operatively connected to the sensor array for providing an alarm signal indicative of an abnormal leg temperature. The method then includes the steps of applying the stocking to the person's leg to cover at least a portion of the person's leg, isolating that leg from external heat exchanger apparatus upon application of the stocking to the person's leg, and automatically and at least periodically monitoring the leg via the sensor array to detect a natural temperature of the leg upon application of the stocking to the person's leg and during continued isolation of the leg from heat exchanger apparatus. The monitored natural leg temperature is automatically compared with at least one temperature threshold. Upon determining that the detected natural leg temperature has moved past the threshold, an alarm signal is automatically generated via the indicator.

According to another feature of the present invention, the alarm signal is a visible alarm signal. In that event, the step of generating the alarm signal may include the step of absorbing a color dye into fabric of the stocking.

It should be noted that the invention contemplates that the wearer of the stocking walks on the leg with the stocking fitted thereto. In that case, the steps of automatically monitoring, automatically comparing, and automatically generating are performed during the walking.

According to another feature of the present invention, the method also comprises the step of automatically applying periodic compressive pressure to the person's leg via the stocking. The application of pressure may include the step of pressurizing a chamber in the stocking with a fluid.

According to a further feature of the present invention, the method additionally comprises the step of exerting a force on the stocking along an upper end thereof to inhibit a rolling down of the stocking. This force may be applied by a strip of soft but substantially rigid polymeric material, extending, for example, longitudinally along the stocking from an edge of a mouth opening thereof.

According to a supplemental feature of the present invention, the method further comprises the step of detecting temperature at a plurality of points spaced from one another along the person's leg. The natural leg temperature is detected at one of the points, the threshold being a temperature detected at another of the points. Alternatively, the threshold may be an average value of a plurality of temperatures detected at a plurality of points spaced from one another along the person's leg.

A medical diagnostic method comprises, in accordance with another conceptualization of the present invention, detecting temperature at a plurality of relatively spaced measurement points on a person's leg, comparing a temperature detected at one of the measurement points with a temperature detected at another measurement point, and providing a signal indicative of a local rise in leg temperature at the one measurement point relative to the other measurement point, thereby providing an alert as to possible phlebitis in the person's leg.

Pursuant to another feature of the present invention, this conceptualization of the invention further comprises the step of comparing the temperature detected at the one measurement point with a plurality of other temperatures detected at a plurality of other measurement points on the person's leg. The temperature detected at the one measurement point may be separately compared with each of the other temperatures. Alternatively, an average value of a plurality of temperatures detected at a plurality of measurement points on the person's leg may be averaged, the temperature detected at the one measurement point being compared with the average value.

A medical stocking with temperature sensing componentry in accordance with the present invention includes plural temperature sensors disposed in an array along and around a person's leg for purposes of detecting a local temperature rise indicative of the inflammation of phlebitis. Such a temperature rise is detected by comparing a skin temperature measured at one point with one or more skin temperatures measured at other points on the leg. Thus, the device can be adapted to the patient's customary body or leg temperature. Temperature comparisons are not made to a fixed, predetermined standard, but to a standard determined by the individual patient.

Inasmuch as skin temperature may rise or fall slightly depending on ambient temperature conditions, the invention serves to compensate for variation in the ambient temperature. In addition, if the patient is walking or otherwise exercising the leg muscles, any resulting rise in skin temperature will be taken into account by the use of multiple sensors and effective averaging techniques.

DETAILED DESCRIPTION

Figure 1:
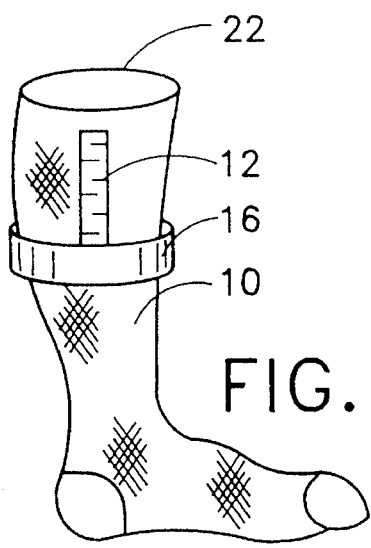
FIG. 1 is a schematic side elevational view of a hospital-type medical stocking with a diagnostic function in accordance with the present invention.
Figure 2:
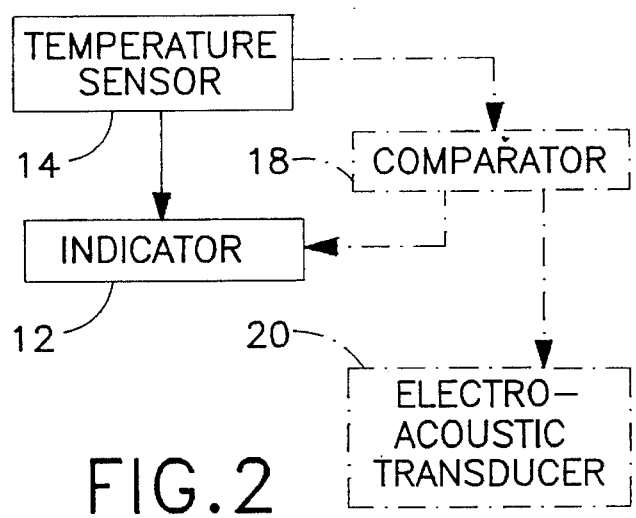
FIG. 2 is a block diagram of operative components of the stocking of FIG. 1.

As illustrated in FIG. 1, a medical diagnostic device comprises a stocking 10 and a temperature indicator 12 attached thereto for providing, to the wearer or to another person such as a hospital attendant, a visual indication of the temperature of the leg to which the stocking is fitted. As illustrated in FIG. 2, the medical diagnostic device further includes a temperature sensor 14 mounted to the stocking 10 and operatively connected mounted to indicator 12. Sensor 14 detects the temperature of the wearer's leg and induces indicator 12 to provide a visual signal indicative of leg temperature.

Temperature sensor 14 may be pressed to the wearer's leg by a band or strip 16 to ensure a heat transmitting contact between the skin and the sensor. Band or strip 16 may be an elastic band. Alternatively, band or strip 16 may be a strip provided with snap-lock fasteners, VELCRO-type hook and loop fasteners, or an adhesive layer. Band or strip 16 is not so tight as to restrict blood circulation in the wearer's leg.

As further illustrated in FIG. 2, temperature sensor 14 is optionally connected to a comparator 18 which compares the sensed temperature with a pre-established threshold. Upon detecting that the temperature has passed the pre-established threshold, comparator 18 induces indicator 12 to provide a visual alert signal. To detect conditions associated with phlebitis, the threshold temperature is an elevated temperature indicative of inflammation.

In a specific implementation of the medical diagnostic device of FIGS. 1 and 2, sensor 14 generates an electrical signal transmitted to comparator 18. Upon detecting, for example, an elevation in leg temperature above a predetermined limit, comparator 18 in turn issues an electrical alarm signal to visual indicator 12 and/or an auditory signal generator or electroacoustic transducer 20.

Alternatively, in a mechanical implementation of the medical diagnostic device of FIGS. 1 and 2, indicator 12 includes a bladder filled with a colored dye (not shown). Sensor 14 operates to rupture or otherwise open the bladder to enable the absorption of the dye into fabric material of stocking 10.

As depicted in FIG. 1, temperature indicator 14 may take the form of a conventional thermometer extending longitudinally along an outer surface of stocking 10 from an upper edge or mouth rim 22 thereof. In that case, temperature indicator 14 also serves to inhibit an undesired rolling down of stocking 10. Preferably, the body of the indicator/thermometer is made of a soft but substantially rigid material.

In using a medical diagnostic device as described hereinabove, stocking 10 is applied to the person's leg to cover at least a portion of the person's leg. Inasmuch as the natural leg temperature is being measured, the leg is naturally isolated from external heat exchangers such as hot or cold water bottles, electric heaters, etc., upon application of stocking 10 to the person's leg. One skilled in the art will recognize that temperature monitoring would not be accurate if the temperature of the leg, or portions thereof, were permitted to rise or fall because of artificial conditions. Naturally, in selecting a standard or reference value for temperature comparison, normal ambient temperature conditions must be assumed.

Temperature sensor 14 automatically and at least periodically monitors the leg to detect a natural temperature thereof upon application of stocking 10 and during continued isolation of the leg from heat exchanger apparatus. Comparator 18 automatically compares the monitored natural leg temperature with at least one temperature threshold (a high temperature value or a low temperature value of a normal temperature range). Upon determining that the detected natural leg temperature has moved past the threshold, comparator 18 induces generation of an alarm signal.

It is contemplated that the wearer of stocking 10 may walk on the leg with the stocking fitted thereto. In that case, the automatic temperature monitoring, the automat comparison, and the automatic alarm signal generation may be performed while the patient or user is walking.

Figure 3:
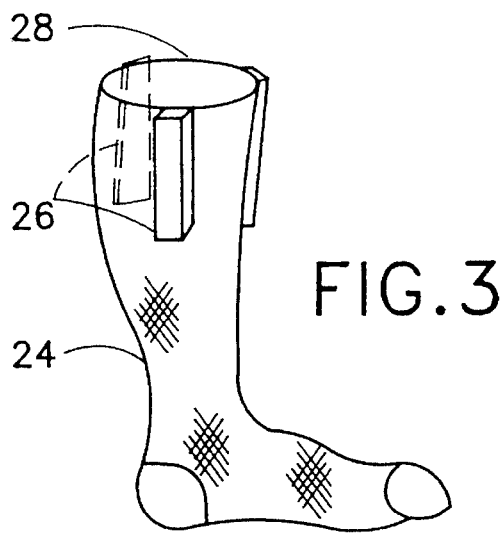
FIG. 3 is a schematic side perspective view of another stocking in accordance with the present invention.

As depicted in FIG. 3, the function of preventing the accidental or inadvertent rolling down of a stocking 24 is implemented by a plurality of strips 26 of a soft but substantially rigid material. Strips 26 preferably extend longitudinally along stocking 24 from an mouth edge or rim 28. Strips 26 may be made of a polymeric material such as polyethylene or polypropylene.

One or more strips 26 may be used in conjunction with indicator/thermometer 14 of FIG. 1.

Figure 4:
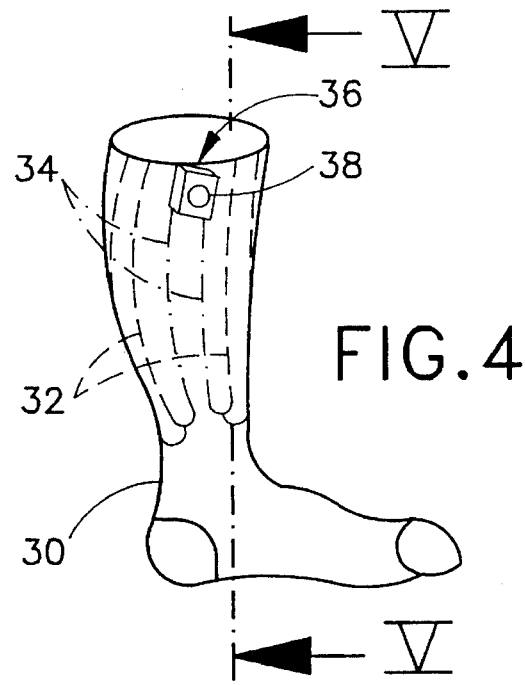
FIG. 4 is a schematic side perspective view of yet another stocking in accordance with the present invention.

As shown in FIG. 4, a stocking 30 is provided with a plurality of longitudinally oriented pressure application chambers 32. At their lower ends, pressurization chambers 32 are connected via respective ducts 34 to a motorized pump 36 attached directly to and carried on stocking 30. Pump 36 operates to periodically pressurize chambers 32 to apply periodic compressive pressure to the wearer's leg. In the event that the pressurization fluid is air, pump 36 has at least one air inlet 38 communicating with the ambient atmosphere. In anticipation of an accidental blocking of inlet 38, several such inlets (not shown) may be spaced from one another along stocking 30. The depressurization of chambers 32 may be accomplished simply by providing outlets 40 (FIG. 6) at the upper ends of pressurization chambers 32.

Figure 5:
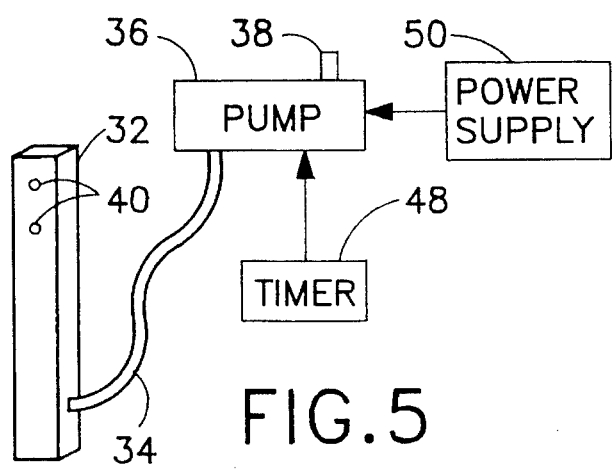
FIG. 5 is a partial longitudinal cross-sectional view taken along line V—V in the stocking of FIG. 4.
Figure 6:
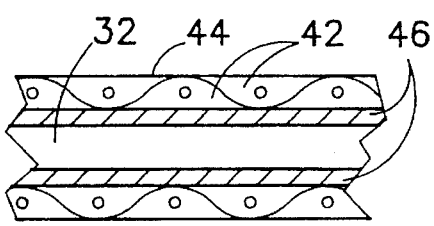
FIG. 6 is a block diagram of operative components of the stocking of FIG. 4.

As illustrated in FIG. 5, stocking 30 further comprises an inner fabric web 42 of substantially elastic material and an outer fabric web 44 of relatively inelastic material. FIG. 6 also shows walls 46 of a pressurization chamber 32 between inner fabric web 42 and outer fabric web 44. The relative tightness of outer web 44 ensures that an expansion of chambers 32 upon pressurization thereof by pump 36 serves to press the leg tissues, rather than merely increasing the circumference or girth of the stocking.

FIG. 6 shows one pressurization chamber 32 and associated inlet duct 34 connected to pump 36. Stocking 30 may also include a timer 48 operatively connected to pump 36 for periodically activating the pump. Also, a power supply 50 connected to pump 36 is attached to and carried on stocking 30.

Figure 7:
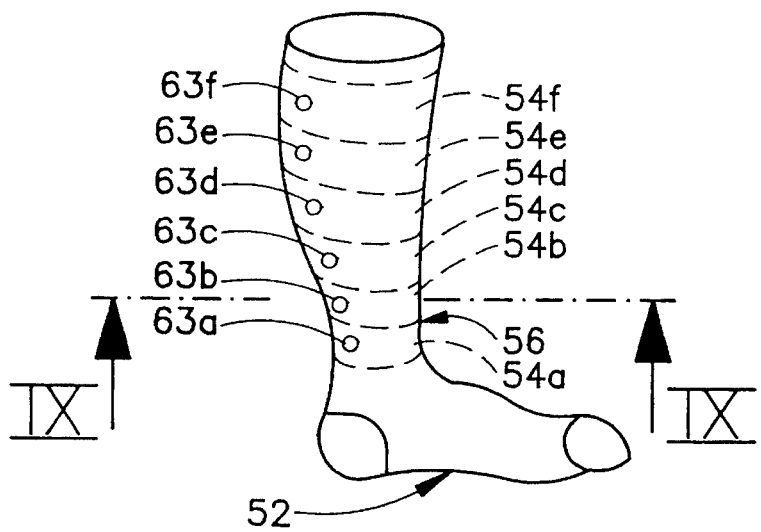
FIG. 7 is a schematic side perspective view of a further stocking in accordance with the present invention.
Figure 8:
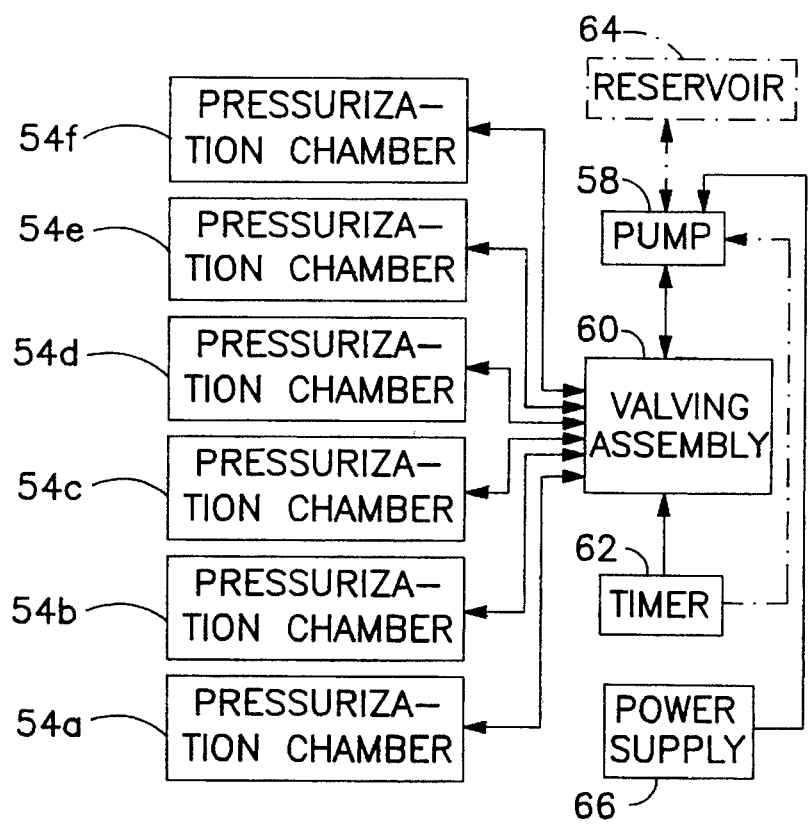
FIG. 8 is a block diagram of operative components of the stocking of FIG. 7.

FIG. 7 depicts a stocking 52 having a plurality of annular pressurization chambers 54a–54f disposed one above the other in a vertical array along the length of the leg portion 56 of stocking 52. As shown in FIG. 8, pressurization chambers 54a–54f are operatively connected to a pressurization pump 58 via a valving assembly 60 controlled by a timer 62. During a cycle of operation of the medical stocking of FIGS. 7 and 8, timer 62 operates to first connect a lowermost pressurization chamber 54a to pump 58 and to subsequently connect adjacent pressurization chambers 54b–54f in succession to the pump. Accordingly, pressure is applied to a wearer's leg from the ankle upwardly towards the knee. This pressurization sequence serves to aid circulation in the veins of the leg and to prevent venous stasis.

Stocking 30 of FIGS. 4–6 also compresses the wearer's leg from the ankle upwardly along the calf, inasmuch as the pressurization of chambers 32 proceeds from the lower ends thereof.

The compression stocking of FIGS. 7 and 8 may operate pneumatically as described hereinabove with reference to FIGS. 4–6. In that event, each chamber 54a–54f may be provided with one or more respective air outlets 63a–63f. Alternatively, the stocking assembly may be provided with a reservoir 64 of a pressurization liquid such as water. With energy provided by a power supply 66 on stocking 52, pump 58 moves pressurization liquid from reservoir 64 to pressurization chambers 54a–54f and back to reservoir 64. Pump 58 may include a reversible motor (not separately illustrated) which is controlled by timer 63. As in the pneumatic case, the sequence of pressurization and depressurization of chambers 54a–54f is controlled by valving assembly 60 in response to signals from timer 62.

Figure 9:
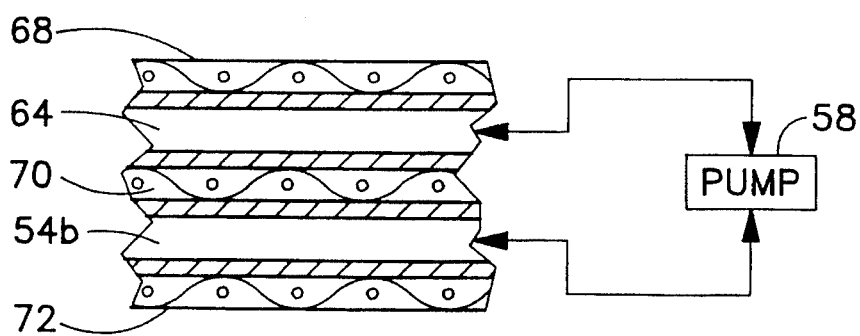
FIG. 9 is partially a partial longitudinal cross-sectional view taken along line IX—IX in FIG. 7 and partially a block diagram.

As illustrated in FIG. 9, stocking 52 includes an outer web 68 of relatively elastic fabric material and a middle web 70 of substantially inelastic material. Reservoir 64 is disposed between webs 68 and 70. Stocking 52 further comprises an inner elastic fabric web 72. Pressurization chambers 54a–54f are disposed between webs 70 and 72. In the event that stocking 52 is pneumatically implemented, resevoir 64 and outer fabric web 68 may be omitted.

Figure 10:
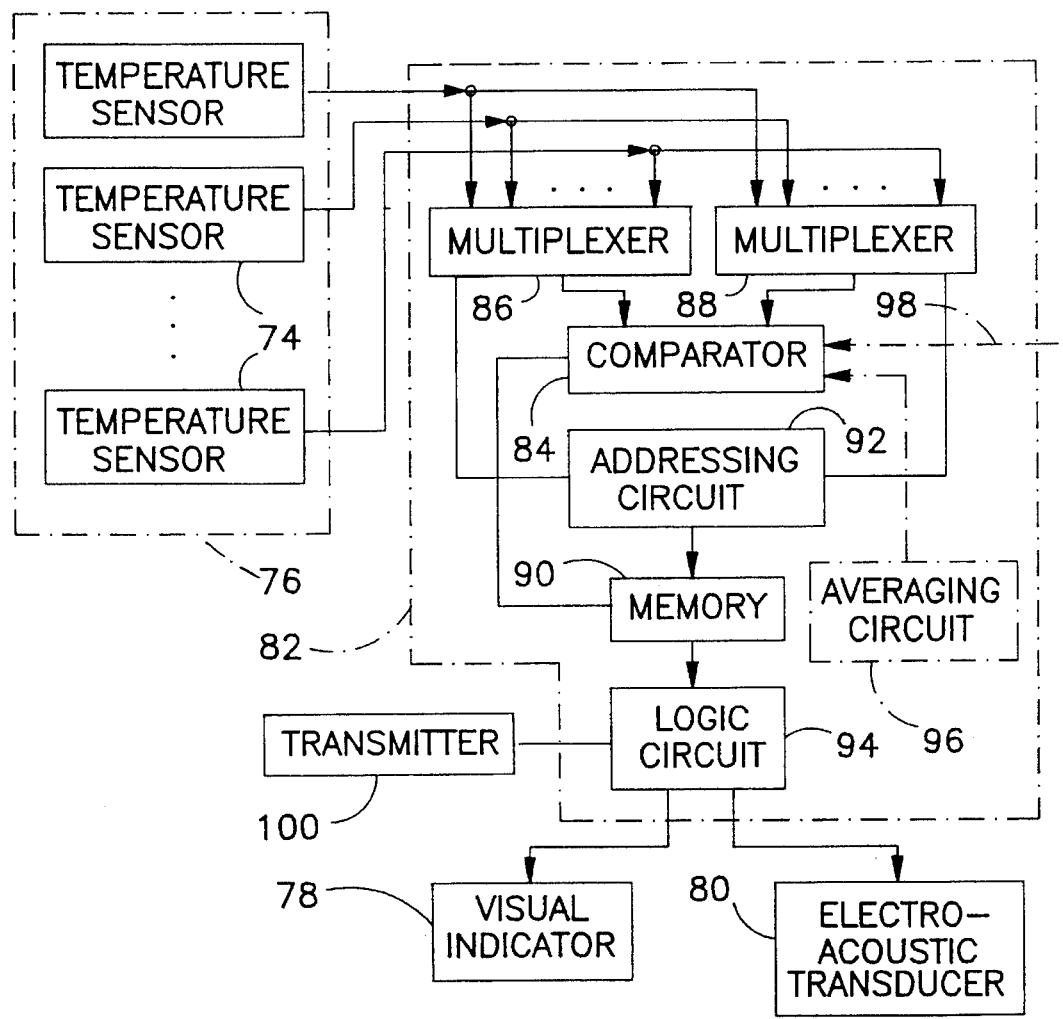
FIG. 10 is a block diagram showing temperature monitoring components of a medical diagnostic device in accordance with the present invention.

As illustrated in FIG. 10, a medical diagnostic device comprises an array of sensors 74 for detecting temperature at a plurality of relatively spaced points on a person's leg. Sensors 74 are mounted to an attachment element 76 in the form of a membrane such as a stocking which is attachable to a person's leg for maintaining sensors 74 in operative juxtaposition with the person's leg. A visual indicator 78 such as a flashing light and an electro-acoustic transducer 80 (an acoustic indicator) are operatively connected to sensors 74 via signal processing circuitry 82 and carried by attachment element 76 for providing a signal indicative of a local rise in leg temperature at one of the measurement points relative to at least one other measurement point, thereby providing an alert or alarm as to possible phlebitis in the leg.

Processing circuitry 82 includes a comparator 84 operatively connected to sensors 74 for comparing a temperature detected by sensor 74 at the one measurement point with a temperature detected by sensors 74 at one or more other measurement points. As further illustrated in FIG. 10, comparator 84 is provided with comparison facilitating componentry in the form of a pair of multiplexers 86 and 88 for enabling a comparison of the temperature detected by sensors 74 at each measurement point separately with the temperature measured by sensors 74 at each of the other measurement points on the person's leg. Comparator 84 generates a signal where a comparison yields a temperature difference greater than a predetermined magnitude. This magnitude is selected to allow for minor variations in skin temperature as a result of normal statistical fluctuations.

The result of each temperature comparison by comparator 84 is stored in a memory 90, in a cell determined by an addressing circuit 92. Addressing circuit 92 is also linked to multiplexers 86 and 88 for sequencing the switching operations thereof.

A logic circuit 94 is connected to memory 90 for scanning the contents thereof. Upon determining that one or more measurement points on the person's leg have temperatures which significantly differ from the temperatures at other measurement points, logic circuit 94 provides an energizing signal to indicator 78 and/or indicator 80. Logic circuit 94 may include a timing unit for ascertaining that a detected temperature difference has persisted over a preprogrammed period, as a condition to energizing indicators 78 and 80.

To implement an alternative mode of operation, processing circuitry 82 includes a calculating circuit 96 operatively connected to sensors 74 for determining an average value of a plurality of temperatures detected by sensors 74 at a plurality of respective measurement points. Comparator 84 receives input from sensors 74 via a single multiplexer 86 or 88 and compares each individual temperature measurement with an average determined by calculating circuit 96. Comparator 84 generates a signal where a comparison yields a difference greater than a predetermined magnitude.

In another alternative mode of operation of processing circuit 82, comparator 84 compares the temperatures detected by sensors 74 at the respective measurement points with a standard or reference value 98 which is provided by a preselected temperature sensor (not separately designated) disposed along a portion of the person's leg which is known not to experience inflammation due to phlebitis. In this mode of operation, as in the other modes of operation of processing circuitry 82, the standard or reference value against which temperature measurements are compared is itself a real time temperature value, rather than a predetermined value.

As additionally illustrated in FIG. 10, a wireless transmitter 100 may be operatively connected to processing circuitry 82 and particularly to logic circuit 94 for generating a wireless signal and transmitting that signal to a monitoring station. Such a station might be at a desk or control room of a hospital. A visual and/or audible signal is produced at the monitoring station for alerting supervisory personnel as to a case of possible phlebitis.

Figure 11:
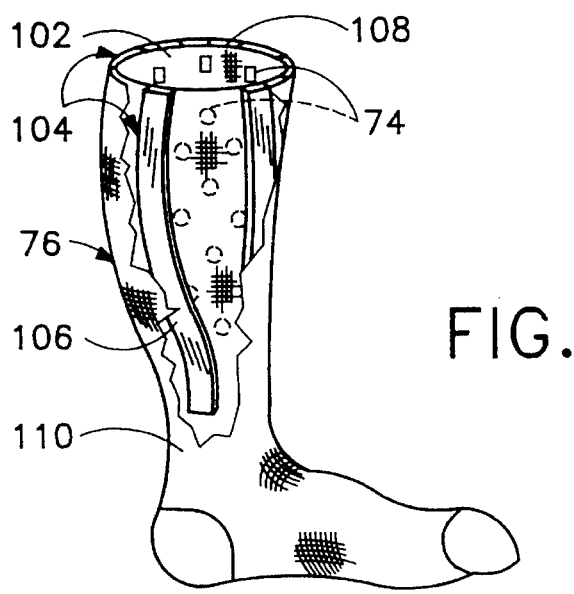
FIG. 11 is a schematic perspective view, partially broken away, of a medical stocking incorporating, inter alia, the temperature monitoring componentry of FIG. 10.

As illustrated in FIG. 11, attachment element 76 includes a flexible membrane 102 in the form of a stocking attachable to a person's leg. This stocking 102 is provided with a plurality of elongate pressurizable chambers 104 each defined in part by strips 106 of soft but substantially rigid polymeric material. Chambers 104 extend longitudinally along stocking 102 from an edge 108 of a mouth opening thereof and serve in part to inhibit an inadvertant rolling down of the stocking. In addition, chambers 104 serve in the automatic application of periodic compressive pressure to the person's leg. As discussed hereinabove with reference to FIGS. 4–6, means are provided for pressurizing chamber 104 with a fluid. Attachment element 76 may also include an outer layer 110 of relatively inelastic material, so that pressurization of chamber 104 directs compressive force inwardly upon the person's leg.

Although the invention has been described in terms of particular embodiments and applications, one of ordinary skill in the art, in light of this teaching, can generate additional embodiments and modifications without departing from the spirit of or exceeding the scope of the claimed invention. For example, equivalent kinds of temperature sensors and indicators may be substituted for sensors 14 and 74 and indicators 12 and 78. In addition, other equivalent designs for pressurization chambers in a stocking in accordance with the present invention are well within the skill of the art. Mechanical pressing devices such as rollers drawn by motors at lower and upper ends of the leg are also within the contemplated scope of the invention. Another equivalent mechanical pressure application assembly includes elongate resilient polymeric strips which are flexed inwardly by one or more motors. Furthermore, with respect to temperature comparison as discussed hereinabove with reference to FIG. 10, it is to be noted that many other equivalent designs of processing circuit 82 will be available, such designs being straightforward engineering alternatives.

Accordingly, it is to be understood that the drawings and descriptions herein are profferred by way of example to facilitate comprehension of the invention and should not be construed to limit the scope thereof.

What is claimed is:

1. A medical diagnostic device comprising:

sensor means for detecting temperature at a plurality of relatively spaced points on a person's leg;

attachment means including a stocking attachable to a person's leg for maintaining said sensor means in operative juxtaposition with the person's leg, said sensor means being mounted to said stocking;

comparator means operatively connected to said sensor means for automatically comparing a temperature detected by said sensor means at one of said points with a temperature detected by said sensor means at another of said points and for generating an electrical signal encoding results of that comparison; and indicator means operatively connected to said sensor means, said stocking and said comparator means for automatically providing, in response to said electrical signal, a sensible signal indicative of a local rise in leg temperature at said one of said points relative to said another of said points, thereby providing an alert as to possible phlebitis in the leg.

2. The device defined in claim 1 wherein said comparator means is provided with additional means for enabling automatic comparison of the temperature detected by said sensor means at said one of said points with a plurality of other temperatures measured by said sensor means at a plurality of other points on the person's leg.

3. The device defined in claim 3 wherein said additional means includes means for comparing the temperature detected by said sensor means at said one of said points with each of said other temperatures individually.

4. The device defined in claim 1, further comprising averaging means operatively connected to said sensor means and said indicator means for determining an average value of a plurality of temperatures detected by said sensor means at a plurality of respective ones of said points, said comparator means being provided with comparison means for comparing the temperature detected by said sensor means at said one of said points with said average value.

5. The device defined in claim 1 wherein said indicator means includes means for providing a visual alarm signal.

6. The device defined in claim 1 wherein said indicator means includes means for providing an auditory signal.

7. A medical diagnostic method comprising the steps of:

providing a medical stocking with sensor means mounted to said stocking for detecting temperature of a person's leg to which said stocking is fitted, said stocking carrying indicator means operatively connected to said sensor means for providing an alarm signal indicative of an abnormal leg temperature;

applying said stocking to the person's leg to cover at least a portion of the person's leg;

upon application of said stocking to the person's leg, automatically and at least periodically monitoring the leg via said sensor means to detect a natural temperature of the leg;

automatically comparing the monitored natural leg temperature with at least one temperature threshold; and upon determining that the detected natural leg temperature has moved past said threshold, automatically generating an alarm signal via said indicator means.

8. The method defined in claim 7 wherein said step of generating includes the step of generating a visible alarm signal.

9. The method defined in claim 8 wherein said step of generating a visible alarm signal includes the step of absorbing a color dye into fabric of said stocking.

10. The method defined in claim 7, further comprising the step of walking on the leg with said stocking fitted thereto, said steps of automatically monitoring, automatically comparing, and automatically generating being performed during said step of walking.

11. The method defined in claim 7, further comprising the step of automatically applying periodic compressive pressure to the person's leg via the stocking.

12. The method defined in claim 11 wherein said step of applying pressure includes the step of pressurizing a chamber in said stocking with a fluid.

13. The method defined in claim 7 wherein said step of generating includes the step of generating an audible alert signal.

14. The method defined in claim 7, further comprising the step of exerting a force on said stocking along an upper end thereof to inhibit a rolling down of said stocking.

15. The method defined in claim 7, further comprising the step of detecting temperature at a plurality of points spaced from one another along the person's leg, said natural leg temperature being detected at one of said points, said threshold being a temperature detected at another of said points.

16. The method defined in claim 7, further comprising the step of determining an average value of a plurality of temperatures detected at a plurality of points spaced from one another along the person's leg, said threshold being said average value.

17. A medical diagnostic method comprising:

providing a medical stocking with sensor means mounted to said stocking for detecting temperature of a person's leg to which said stocking is fitted, said stocking carrying indicator means operatively connected to said sensor means for providing an alarm signal indicative of an abnormal leg temperature;

applying said stocking to the person's leg to cover at least a portion of the person's leg;

upon application of said stocking to the person's leg, detecting temperature at a plurality of relatively spaced points on the person's leg via said sensor means;

automatically comparing a temperature detected at one of said points with a temperature detected at another of said points; and automatically providing a signal indicative of a local rise in leg temperature at said one of said points relative to said another of said points, thereby providing an alert as to possible phlebitis in the person's leg.

18. The method defined in claim 17, further comprising the step of comparing the temperature detected at said one of said points with a plurality of other temperatures detected at a plurality of other points on the person's leg.

19. The method defined in claim 17, further comprising the step of separately comparing the temperature detected at said one of said points with each of a plurality of other temperatures detected at a plurality of other points on the person's leg.

20. The method defined in claim 17, further comprising the step of determining an average value of a plurality of temperatures detected at a plurality of other points on the person's leg, said step of comparing including the step of comparing the temperature detected at said one of said points with said average value.

21. A medical diagnostic device comprising:

sensor means for detecting temperature at a plurality of relatively spaced points on a person's leg;

attachment means including a flexible membrane attachable to a person's leg for maintaining said sensor means in operative juxtaposition with the person's leg, said sensor means being mounted to said attachment means;

means on said membrane for inhibiting a rolling down thereof; and indicator means operatively connected to said sensor means and to said attachment means for providing a signal indicative of a local rise in leg temperature at one of said points relative to another of said points, thereby providing an alert as to possible phlebitis in the leg.

22. The device defined in claim 21 wherein said means for inhibiting includes a strip of soft but substantially rigid material.

23. The device defined in claim 22 wherein said strip extends longitudinally along said membrane from an edge of a mouth opening.

24. The device defined in claim 22 wherein said strip is made of polymeric material.

25. A medical diagnostic device comprising:

sensor means for detecting temperature at a plurality of relatively spaced points on a person's leg;

attachment means including a flexible membrane attachable to a person's leg for maintaining said sensor means in operative juxtaposition with the person's leg, said sensor means being mounted to said attachment means;

pressure application means on said membrane for automatically applying periodic compressive pressure to the person's leg; and indicator means operatively connected to said sensor means and to said attachment means for providing a signal indicative of a local rise in leg temperature at one of said points relative to another of said points, thereby providing an alert as to possible phlebitis in the leg.

26. The device defined in claim 25 wherein said pressure application means includes at least one chamber and means for pressurizing said chamber with a fluid.

27. The device defined in claim 26 wherein said membrane includes an outer layer of relatively inelastic material, whereby pressurization of said chamber directs compressive force inwardly upon the person's leg.

28. A medical diagnostic device comprising:

sensor means for detecting temperature at a plurality of relatively spaced points on a person's leg;

attachment means including a foot stocking attachable to a person's leg for maintaining said sensor means in operative juxtaposition with the person's leg, said sensor means being mounted to said stocking; and indicator means operatively connected to said sensor means and to said stocking for providing a signal indicative of a local rise in leg temperature at one of said points relative to another of said points, thereby providing an alert as to possible phlebitis in the leg.

* * * * *